United States Patent [19]

Jolson et al.

[11] Patent Number: 5,094,521
[45] Date of Patent: Mar. 10, 1992

[54] APPARATUS FOR EVALUATING EYE ALIGNMENT

[75] Inventors: Alfred S. Jolson, Maitland; Harley R. Myler; Arthur Weeks, both of Orlando, all of Fla.

[73] Assignee: Vision Research Laboratories, Winter Park, Fla.

[21] Appl. No.: 610,030

[22] Filed: Nov. 7, 1990

[51] Int. Cl.⁵ .............................................. A61B 3/14
[52] U.S. Cl. ................................. 351/210; 351/206; 351/246
[58] Field of Search ............... 351/209, 210, 206, 207, 351/208, 239, 243, 246; 128/145

[56] References Cited

U.S. PATENT DOCUMENTS

| 4,528,989 | 7/1985 | Weinblatt et al. | 351/210 X |
| 4,648,052 | 3/1987 | Friedman et al. | 351/210 X |
| 4,789,235 | 12/1988 | Borah et al. | 351/210 X |
| 4,859,050 | 8/1989 | Borah et al. | 351/210 |

Primary Examiner—Rodney B. Bovernick
Attorney, Agent, or Firm—William M. Hobby, III

[57] ABSTRACT

An apparatus for evaluating the alignment of both eyes of a patient objectively in primary, secondary and tertiary gaze, and the Bielschowsky head tilt positions and to diagnose for phorias, tropias and intermittent tropias. The apparatus has a head restraint and a mounted fixation target in a spaced relationship to the head restraint and having adjustments for adjusting the target along three axis. Electronic shutters are used to occlude each eye during the testing. A camera is used for imaging the eye of a patient having his head in the head restraint with his eyes aligned with the target. The camera is mounted adjacent to the target on the xyz mount. A micro-computer has a monitor screen, and is operatively coupled to the camera for receiving a series of images from the camera stored data for each frame, and comparing one frame image with another frame image of the same eye and gaze position or both eyes in the same frame to thereby determine a patient's ocular alignment, pupil size, corneal diameter and interpupillary distance.

17 Claims, 3 Drawing Sheets

APPARATUS FOR EVALUATING EYE ALIGNMENT

BACKGROUND OF THE INVENTION

The present invention relates to an automated electronic instrument that will rapidly evaluate the alignment of both eyes objectively in primary, secondary and tertiary gaze, and the Bielschowsky head tilt positions and diagnose for phorias, tropias and intermittent tropias.

The present invention is referred to as a Trophorometer because it will measure tropias (manifest ocular misalignment) and phorias (latent deviation compensated for by the fusional reflex) to within one to two degrees. Computer image processing technology allows the measurement of the strabismus and obviates the use of prisms with their many shortcomings.

The present invention allows for screening for eye misalignment (eye muscle imbalance) by eye practitioners and to aid in the diagnosis of strabismus and to gauge treatment.

The eye alignment exam is an integral part of the routine eye examination performed by the eye specialist. Besides poor cosmesis, eye misalignment can be a cause for monocular visual loss (amblyopia), impaired binocular perception, reading difficulties, headaches, double vision, dizziness, nausea, and ocular toticollis (head tilt). Eye misalignment can also be a manifestation of a systemic disorder such as diabetic ocular neuropathy, thyroid eye disease, myasthenia gravis, child abuse/trauma, or a neurological disorder such as a cranial nerve palsy secondary to an intracranial lesion. In children, eye misalignment may be a presenting sign of a congenital cataract, or a life threatening eye tumor, a retinoblastoma. Proper diagnosis can enable the eye practitioner to initiate the appropriate surgical, optical, or medical treatment for the strabismus.

There are subjective and objective tests for measuring strabismus. Subjective methods involving patient response use dissimilar image or dissimilar target tests. Dissimilar image tests are based on the patient's response to diplopia produced by converting an isolated object of regard into different images of each retina (i.e. haploscope, Lancaster Red-Green Projectors). In these methods, the credibility of the results depends upon the skill of the examiner, the cooperation of the patient, and the existence of normal retinal correspondence without dense amblyopia or suppression.

The objective tests currently in use to evaluate eye alignment are based upon observing either the positions of the corneal light reflexes (Hirschberg and Krimsky Tests) or detecting eye refixation movements during occlusion and its removal (prism and cover test and the haploscope).

Other light reflexes such as the Purkinjie reflexes are used to track eye motions (Dual Purkinjie Eyetracker, SRL) and the red reflex to detect refractive differences between the eyes and gross misalignment. Other instruments make physical contact with the globe and measure eye movement but not eye position (EOG, ENG, Robinson Scleral Coil, force measuring forceps). The Nakayama photographic method measures small deviations with globe markers. A computer patient interaction system, the Computer Ocular Torsion Test, measures cyclotorsion deviation.

In the present invention, the Trophorometer will not only examine for small or large angle ocular deviations, but will also record pupil size, corneal diameters, lid fissure heights, interpupillary distance, and axial length. This ancillary information is of value to the eye practitioner for fitting contact lenses, sizing anterior chamber lenses, evaluating ptosis, fitting glasses, and planning eye muscle surgery for infantile esotropia.

The results of eye muscle balance testing performed as part of a routine eye examination generally depends on the skill of the examiner. It takes a trained observer to diagnose and measure tropias and phorias. Measurement of strabismus on the same patient can vary even between experienced examiners. There is no commercially available automated electronic instrument in ophthalmology to perform an eye alignment examination as there are computerized automated instruments to do visual fields, measure corneal curvatures, and do refractions.

Essentially, the present system consists of an electronic (CCD) camera set 33 cm in front of the patient that is level with, and midway between the eyes. Standard cover/uncover and alternate cover testing is done with the seated patient fixating on a small accommodative target in the center of the camera lens while secured in a special headrest. A sequence of images is captured and stored by an IBM compatible AT class computer. Change in position of each eye is compared in subsequent picture frames by the computer using an image processing algorithm that determines the direction and amplitude of the deviation and renders a diagnosis expressed in prism diopters and/or degrees.

SUMMARY OF THE INVENTION

This is an apparatus for evaluating the alignment of both eyes of a patient objectively in primary, secondary and tertiary gaze, and the Bielschowsky head tilt positions and to diagnose for phorias, tropias and intermittent tropias. The apparatus has a head restraint and a mounted fixation target in a spaced relationship to the head restraint and having adjustments for ajusting the target along three axis. A camera is used for imaging the eye of a patient having his head in the head restraint with his eyes aligned with an accommodation target mounted at the center of the camera lens. A set of computer controlled calibration lamps (targets) are mounted around the camera lens. A micro-computer has a monitor screen, and is operatively coupled to the camera for receiving a series of images from the camera stored data for each frame, and comparing one frame image with another frame image of the same eye and gaze position to thereby determine a patient's ocular alignment, pupil size, corneal diameter and interpupillary distance. Computer controlled shutter panels occlude the patient's vision in either eye during the testing sequence.

BRIEF DESCRIPTION OF THE DRAWINGS

Other objects, features and advantages of the present invention will be apparent from the written description and the drawings in which.

DESCRIPTION OF THE PREFERRED EMBODIMENTS

Figure 1:
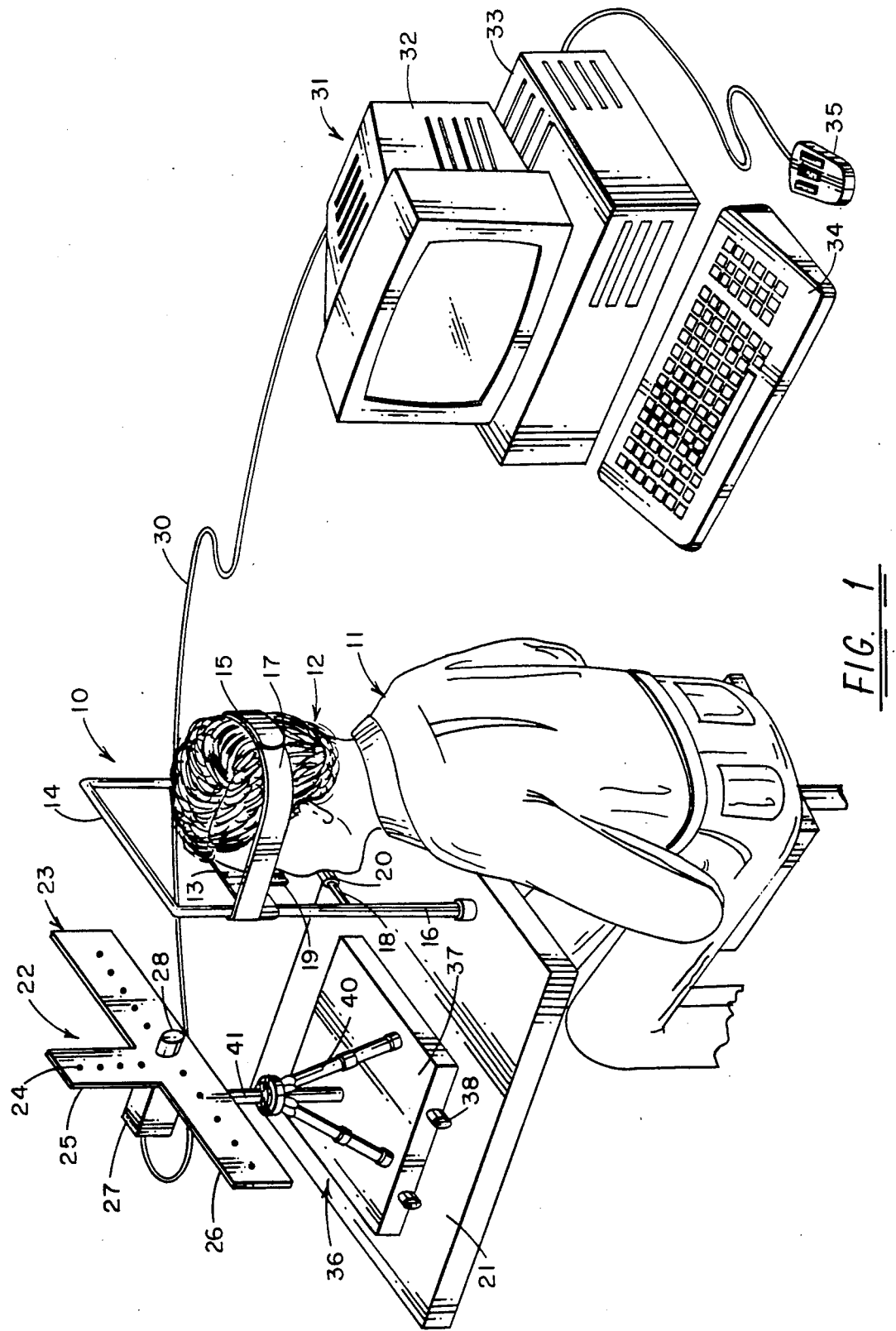
FIG. 1 is a perspective view of a Trophorometer in accordance with the present invention.

Referring to the drawing, FIGS. 1 through 5, a Trophorometer apparatus 10 for evaluating the alignment of both eyes of a patient is illustrated. In FIG. 1 a patient 11 is being tested and has his head 12 placed against an alignment bar 13 of a frame brace 14. The head is held in position by a strap 15 connected to the frame brace members 16 and extending around the head 12 and held in place with VELCRO fastners 17. The patient's mouth is held on a bite bar 18 having a replacable resielient bite member 20. The frame patient brace 14 is attached to the frame base 21.

Figure 4:
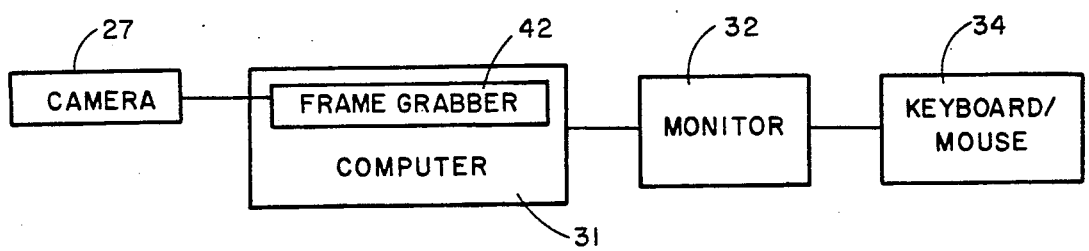
FIG. 4 is a block diagram of the computer system of the present invention.

The frame base 21 has the target assembly 22 attached thereto having the target 23 thereon having a plurality of target spots 24 aligned in predetermined locations on a vertical target member 25 and on a horozontal target member 26. The distance between the central target and the patient 11 is 33 centimeters. A CCD camera 27 is mounted to the back of the target 23 with the lens 28 protruding through the center of the target and aimed directly at the patient 11. The camera may be fitted with a 25 mm 0.95 f-stop lens that provides a 10 mm depth of field at the standard evaluation distance of 33 cm. A cable 30 connects the camera 27 to a personal computer 31 having a monitor 32 having a CPU 33, a keyboard 34 and a mouse 35. Any computer can be used but an MS-DOS computer using and Intel 80386 microprocessor and a VGA monitor and an 80 megabyte hard disk meets the requirements for rapid processing and display in a graphic mode. As seen in FIG. 4, the camera 27 connects directly to a frame grabber circuit board 42 in the computer 31 with the computer connected to the monitor 32 and keyboard 34 and mouse 35.

The target 23 and camera 27 is supported to the base 21 with a three axis (x, y, & z) support assembly 36 having a vernier controlled stand 37 with y and z axis vernier dials 38 and a base tri-pod 40 having a x axis adjustment through the crank raised and lowered center shaft 41.

In operation a patient 11 is connected to the head brace 14 as shown strapped with the headstrap 15 and biting on the bite bar 18. This postions his eyes properly and steady for the examination. The patient is directed to stare at predetermined target spots 24 and images are made with the camera 27. Two clear liquid crystal panels 19 that extend across the visual axis of each eye are located in front of the patient's eyes. Fixation of either eye can be occluded during the testing by darkening either computer controlled electronic liquid crystal panel. The images are stored in the computer 31 in digital format for processing and display. The computer system determines eye position and topographic features from images of the eyes that it acquires from the patient. Installed in the computer 31 is a Coreco Occulus 300 image processing system (frame grabber 42) that is used to digitize images from the camera and store them on the hard disk. A computer program is used as an interactive image analyzer that allows the user complete control over the imaging system. This control includes image digitization from the camera 27, image storage and retrieval from either hard disk or floppy, liquid crystal panel shutter control and image analysis. This program determines the data required for verifying the strabismus algorithms. The second program automatically locates the pupils of eyes in an image set (an image set consists of one image with four pairs of eyes) called a frame.

Figure 2:
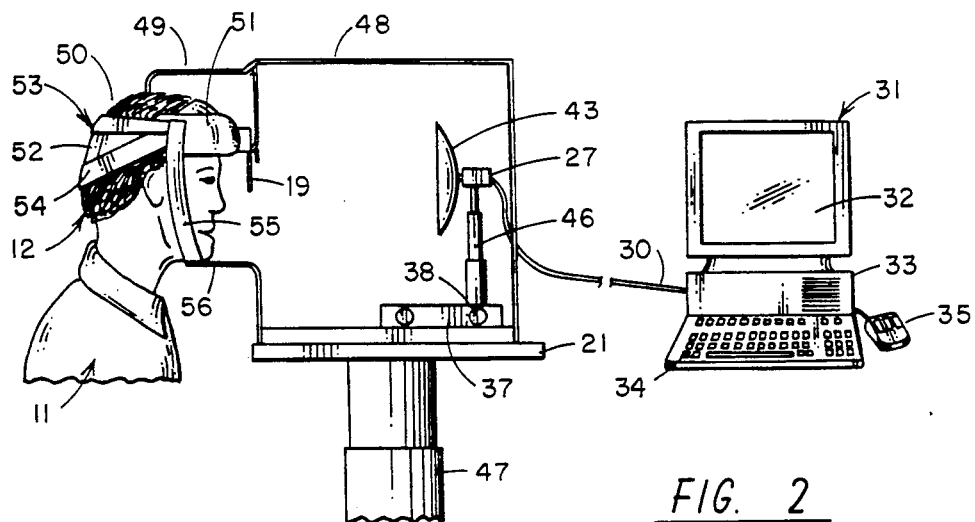
FIG. 2 is a side elevation of a modified embodiment of FIG. 1.
Figure 3:
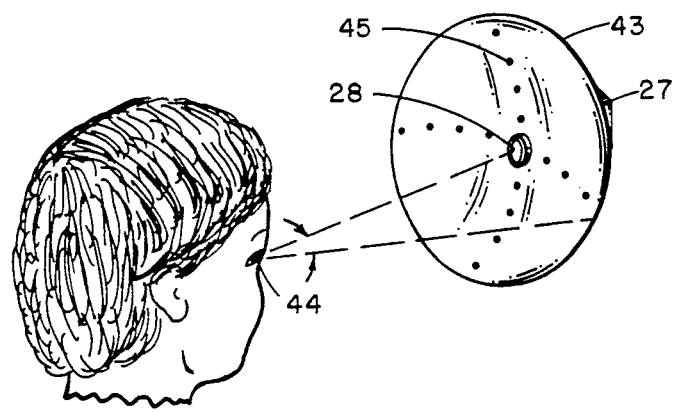
FIG. 3 is a perspective view of a patient target alignment in accordance with FIG. 2.

Referring to FIGS. 2 and 3 the system of FIG. 1 is illustrated except the target is a dish target 43 which controls the distance from the patient's eyes 44 to the target spots 45. In addition the tripod has been replaced with a monopod 46 x-axis adjustment setting on the base 37. The frame base 21 is seen supported by a table leg 47 which may also be adjustable to position the height of the apparatus. The cable 30 and the computer 31, monitor 32, CPU 33 and keyboard 34, and mouse 35 are also shown in FIG. 2. The patient's head 12 is held with a different head support 50 which eliminates the bite bar 18 and has an arcuate head support member 51 having a pair of head straps 52 and 53 with VELCRO fastners 54. A chin strap 55 is also connected from the head brace 51 around the patient's chin 56. Two clear liquid crystal panels 19 extend across the visual axis of each eye and are actuated by an electrical signal from the computer to act as an electronic shutter by blocking the gaze of one or the other eye during examination.

Figure 5:
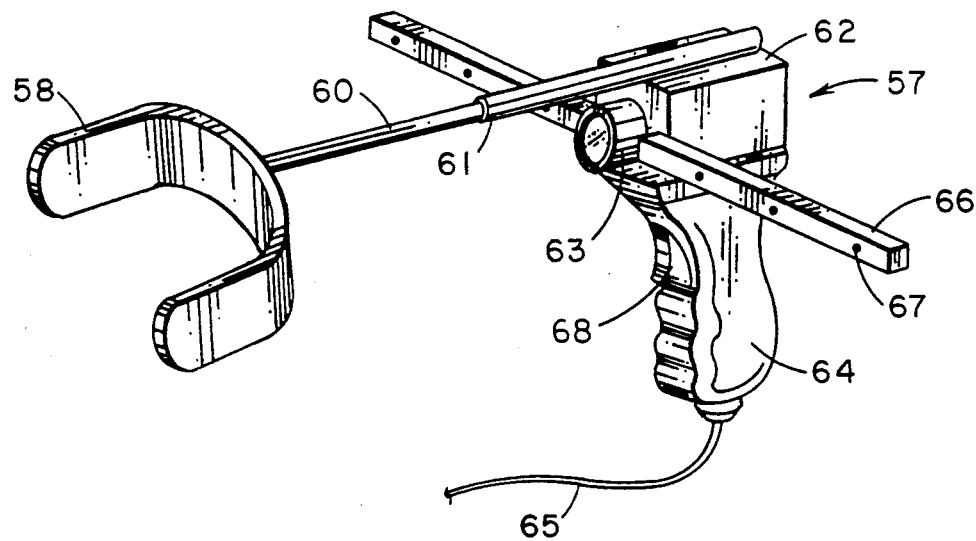
FIG. 5 is perspective view of an alternate embodiment of a hand held Trophorometer in accordance with the present invention.

A portable Trophorometer is 57 is illustrated in FIG. 5 having an arcuate head brace 58 attached to a spacing rod 60 which is telescopingly adjustable and has a lock screw 61. The rod 60 is attached to the camera 62 having a lens 63 and a handle 64 and connected to a computer 31 by a cable 65. A target 66 has spaced target spots 67 thereon. The camera 62 has a trigger 6 in the handle 64.

When the apparatus is initially activated by applying power, the computer automatically initializes itself through a system boot program. Then, via the autoexec.bat batch file, a standard mechanism for autoloading programs, the program is loaded and run by the computer. The main program consists of a number of subparts, or process sequences described hereinafter.

The initialization process consists of three subroutines that are called in sequence by the main program. The first simply places a logo graphic on the computer display to indicate to the operator that the program has been loaded and is running. The second subroutine verifies that the camera, the apparatus fixture, and the image processor are attached and responding correctly to test sequences. The third subroutine activates the dynamic memory allocation required by the data collection routines and reads a history file from the disk. The history file contains a descriptive data structure indicating user selectable states from the previous activation session with the apparatus.

The select mode follows initialization. A menu is displayed on the computer screen allowing the operator to select the mode using either the keyboard or the mouse.

The manual mode allows the operator to retrieve patent images and analyze them directly using the mouse to indicate data points and regions on the screen. A range of standard image analysis commands are made available for the use of the advanced user as well as access to the special subroutines used by the strabismus exam mode to locate the eye topographical features.

The strabismus exam mode performs the basic strabismus analysis process for collection of the patient data and evaluation of eye position. The mode begins by requesting that the operator input the patient identification data (name, age, etc.) or select a known patient from the database. The computer tests for whether the handheld form of the apparatus is being used or the table top version. If the hand-held version is being used, the operator need only squeeze the trigger button mounted to the handgrip and the data acquisition sequence is stepped automatically. Otherwise, the operator is instructed to insure that the patient is secured into the instrument and pressure sensors in the head restraint 51 are accessed by the computer to verify that a patient is restrained and not moving.

The exam begins with the computer activating selected calibration lamps and digitizing the patient's gaze after fixation. Fixation is indicated to the computer by the operator either by keyboard input (spacebar), mouse button, or pistol-grip trigger if the hand-held unit is in use. The selection of the sequence and number of calibration lamps to use is determined by the operator depending on the age and maturity of the patent and the degree of accuracy desired. The computer stores the digitized calibration images in sets of four subframes for later processing. Each of the subframes is 120 lines of 512 pixels. This corresponds to a full image of 480 lines of 512 pixels.

After the calibration images are digitized, the computer activates a sequence of lamps to attract the gaze of the patient. Each time this occurs, the computer digitizes the patient gaze. At specific times determined by the strabismus algorithm, the left or right eye of the patient may be occluded through the use of a liquid crystal shutter panel. The shutter panel is rectangular in shape and mounted within the apparatus at eye level. The panel is divided into a right and left half that can be made transparent or opaque under computer control. This action is necessary in order that the motion of the eye, if any, can be recorded after an uncover sequence.

The image processing algorithms begin with an edge detection processed over the entire image (four eye pair frames) to extract the edges of the pupil, limbus, and fissure outline of each eye.

This is followed by a horizontal and vertical maximum detector that determines the best ridge line along the extracted edges. This algorithm is also known as a moving window thinning technique, the window is set at 32 pixels.

A circular Hough transform is then applied to locate the pupils. The accumulator space of the Hough is restricted to find circles between 5 and 50 pixels in diameter and this corresponds to pupil sizes of one to ten millimeters. The detection of the pupils also yields pupil center coordinates that are used in the strabismus algorithm to measure ocular deviation.

The computer controls a small lamp located within the center of the camera lens called the angle kappa lamp. The eye pairs digitized while illuminated with the angle kappa lamp are processed for the location of the maximum intensity within the pupil area when the patient is fixated on the lamp. This reveals the coordinates of the light reflex and is processed by the strabismus algorithm to determine angle kappa.

The system then processes corneal diameter using the Hough circle finding algorithm by starting with a circle of the maximum possible cornea size (approx. 13 mm) until it reaches the edge corresponding to the patient cornea. This set of search circles are centered at the center coordinate (centroid) determined for the pupil.

The upper and lower projected corneal edge on the vertical axis (hidden under the lids) evaluates pixels along the axis towards the pupil centroid until the inner edges (top and bottom) of the fissure are located. The pixel distance between these points yield fissure height.

Angle kappa, corneal diameter, and fissure height are only processed once during the strabismus exam mode. Detection and location of the pupil is repeated for all phases of the strabismus algorithm.

The diagnose mode invokes the expert diagnosis program (artificial intelligence) that uses the diagnosis data determined from the strabismus exam mode and suggests treatment based on human expert experience in strabismus evaluation. It operates independent of the other machine modes and does not require that the patient fixture be operational or present. This mode can accept patient strabismus data from a computer file created during the strabismus exam mode, or data can be input from the keyboard by the operator. The diagnose mode should not be confused with the diagnostic algorithm. The diagnostic algorithm evaluates the pupil position data to determine the presence and degree of strabismus. The diagnose mode uses this diagnosis to suggest a treatment.

In the strabismus algorithm, the patient is instructed to look at the target (angle kappa lamp) suspended centrally 15 mm in front of the lens in the lens barrel. Then the cover/uncover procedure is performed. Frames (FRM) are stored for the cover/uncover sequence. Cover means that the computer causes the liquid crystal shutter to become opaque.

In the evaluation of strabismus with the apparatus, sequential pictures of each eye undergoing cover/uncover testing are compared to each other. Thus, the position of the right eye is compared separately to sequential cover/uncover positions of the right eye. Identical comparisons are made for the left eye.

The apparatus uses three types of cover/uncover tests that correspond to the clinical prism and cover tests. The first test (I) used by the apparatus is a cover test and clinically corresponds to the simultaneous prism and cover test. It is named the Simulated Simultaneous Prism and Cover Test (SSP&C) and measures for tropia only. The second test (II) used by the apparatus is a cover/uncover test and clinically corresponds to the Prism and Cover Test. It is named the Simulated prism and Cover Test (SP&C) and measures the phoria plus tropia. The third test (III), the Alternate and Cover Test (A&C), is the same clinical test for the apparatus. It measures the maximum deviation.

The Binocular Fixation Pattern (BFP) test determines the preferred eye for fixation.

Angle Kappa is measured with the right eye then the left eye fixating.

Figure 6:
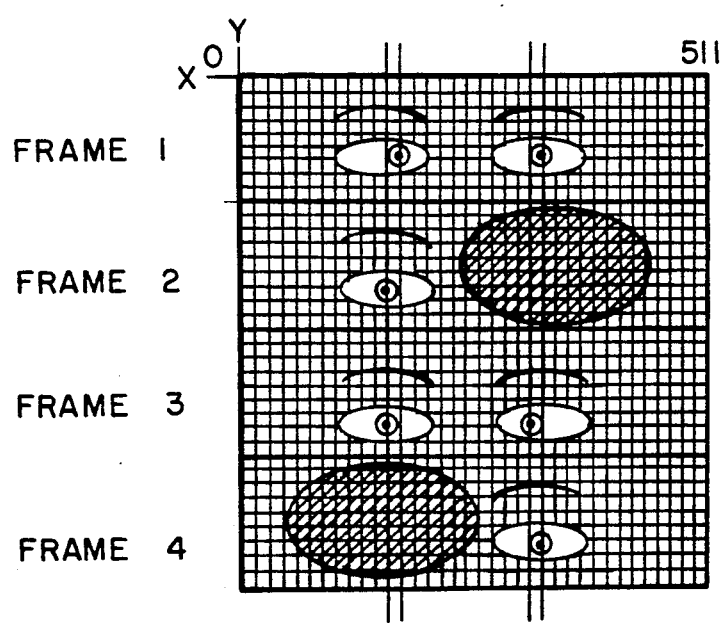
FIG. 6 illustrates the four frames of an image as seen on the apparatus monitor.

FIG. 6 illustrates the four frames of an image as seen on the apparatus monitor and explains the location of the coordinates (x, y) of a point. Horizontal and vertical coordinate values for the pupils in each subframe of this figure are shown. These values are determined by the strabismus analysis program and submitted to the diagnostic algorithm to evaluate whether strabismus is present and to what degree.

The apparatus monitor screen consists of a grid of horizontal (512) and vertical (480) lines. Each square, known as a picture element, or pixel, has x (horizontal) and y (vertical) coordinates. A total of four frames (each 512 × 120 pixels) each containing a picture of both eyes can be displayed on the screen. The coordinates for the center of the pupil of an eye are located in one frame and compared to the coordinates of the center of the pupil for the same eye in another frame. The amount and direction of change in position of the eye, if any, is determined by the difference in the pixel count. The relationship of the pixel count to deviations in physical clinical parameters such as degrees or diopters is a function of the calibration portion of the strabismus exam.

All frames are digitized and then the pupil positional analyses are made. The computer results of the eye positions from frame to frame are used with the if-then rules in the diagnostic algorithm. This algorithm is based on what eye deviations mean in clinical terms.

We claim:

1. A Trophorometer to evaluate the alignment of a patient's eye comprising:
   head positioning means for spacing the head of a patient in a predetermined position;
   a target;
   target mounting means for adjustably mounting said target relative to said head restraint and having adjustments for adjusting said target along three axes;
   camera means for simultaneously imaging both eyes of a patient having his head in said head restraint with said eyes aligned with said target, said camera means being mounted adjacent said target in alignment with the patient's eyes; and
   computer means including a monitor screen, said computer means being operatively coupled to said camera means for receiving a series of images from said camera means stored data for each frame, comparing one frame image with another frame image of the same eye and gaze position to thereby determine a patient's eye alignment, pupil size, corneal diameter and interpupillary distance.

2. A Trophorometer in accordance with claim 1 in which said target includes a pair of intersecting rows of gaze points thereon.

3. A Trophorometer in accordance with claim 2 in which said target has a generally dish shape having said gaze points thereon.

4. A Trophorometer in accordance with claim 3 in which said camera means has a lens mounted through said target and aimed at a patient's head.

5. A Trophorometer in accordance with claim 4 in which said head positioning means includes a head restraint having a frame and a head strap for holding a patient's head facing said target.

6. A Trophorometer in accordance with claim 5 in which said target mounting means includes an X-Y vernier mechanism for adjusting said target in an X-Y direction.

7. A Trophorometer in accordance with claim 6 in which said target mounting means includes a vertical adjustment means for vertical adjustment of said target.

8. A Trophorometer in accordance with claim 1 in which said computer means activates said camera means to produce a plurality of graphic images of a patient's gaze fixed upon selected gaze points.

9. A Trophorometer in accordance with claim 8 in which said target gaze points includes a plurality of lights mounted on said target, said plurality of lights being activated selectively by said computer means to determine the plurality of gaze points for said graphic images.

10. A Trophorometer in accordance with claim 1 in which at least one electrical shutter is positioned in front of said head positioning means for blocking the gaze of one eye of a patient during examination.

11. A Trophorometer in accordance with claim 10 in which a liquid crystal panel is positioned in front of said head positioning means for blocking the gaze of one eye of a patient during examination.

12. A Trophorometer in accordance with claim 11 in which a pair of liquid crystal panels are positioned in front of said head positioning means for selectively blocking the gaze of either eye of a patient during examination.

13. A method of evaluating the alignment of a patient's eyes comprising the steps of:
   restraining a patient's head in a head restraint in a predetermined position relative to a gaze target;
   adjusting a gaze target position relative to a patient's head;
   imaging both eyes simultaneously of a patient having his head restrained in said head restraint with said eyes in a fixed gaze upon predetermined target gaze points with a camera mounted adjacent said target;
   sending said eye images from said camera to a coupled computer having a monitor screen, said computer being operatively coupled to said camera means for receiving a series of images from said camera means stored data for each frame; and
   comparing one frame image of a pair of eyes with another frame image of the same pair of eyes and gaze position to thereby determine a patient's eye alignment, pupil size, corneal diameter and interpupillary distance.

14. A method of evaluating the alignment of a patient's eyes in accordance with claim 13 including the step of activating said camera with said computer to produce a plurality of graphic images of a patient's gaze fixed upon selected gaze points.

15. A method of evaluating the alignment of a patient's eyes in accordance with claim 14 including the step of activating selective ones of a plurality of gaze point lights on said target with said computer to determine a plurality of gaze points for a patient's graphic images.

16. A method of evaluating the alignment of a patient's eyes in accordance with claim 13 including the gaze of a patient's eye during an examination.

17. A method of evaluating the alignment of a patient's eyes in accordance with claim 16 including the step of selectively blocking the gaze of a patient's eye by activating a liquid crystal panel in front of a patient's eyes during examination.

* * * * *